United States Patent [19]

Kalopissis

[11] 4,151,301

[45] * Apr. 24, 1979

[54] ORALLY ADMINISTERED COMPOSITION CONTAINING ORGANIC AMINE-ORGANIC ACID ADDITION SALT FOR REDUCING EXCESSIVE SECRETION OF SEBUM ON HUMAN SKIN AND SCALP

[75] Inventor: Gregoire Kalopissis, Paris, France

[73] Assignee: L'Oreal, Paris, France

[*] Notice: The portion of the term of this patent subsequent to Apr. 22, 1992, has been disclaimed.

[21] Appl. No.: 737,192

[22] Filed: Oct. 29, 1976

Related U.S. Application Data

[60] Division of Ser. No. 534,804, Dec. 20, 1974, Pat. No. 4,002,671, which is a division of Ser. No. 203,038, Nov. 29, 1971, Pat. No. 3,879,560, which is a continuation-in-part of Ser. No. 801,840, Feb. 24, 1969, abandoned, Ser. No. 858,161, Sep. 15, 1969, Pat. No. 3,671,643, Ser. No. 12,122, Feb. 17, 1970, abandoned, and Ser. No. 36,405, May 11, 1970, abandoned, said Ser. No. 858,161, is a continuation-in-part of said Ser. No. 801,840, Ser. No. 817,193, Apr. 17, 1969, abandoned, and Ser. No. 736,960, Jun. 14, 1969, abandoned, which is a continuation-in-part of Ser. No. 427,976, Jan. 25, 1965, abandoned, and Ser. No. 602,480, Dec. 19, 1966, abandoned.

[30] Foreign Application Priority Data

| Dec. 22, 1965 [LU] | Luxembourg | 50125 |
| Feb. 23, 1968 [LU] | Luxembourg | 55553 |
| Apr. 19, 1968 [LU] | Luxembourg | 55935 |
| Feb. 19, 1969 [LU] | Luxembourg | 58042 |
| May 12, 1969 [LU] | Luxembourg | 58634 |
| Oct. 28, 1971 [LU] | Luxembourg | 64174 |

[51] Int. Cl.$^2$ ............................................. A61K 31/205
[52] U.S. Cl. ................................. 424/316; 260/501.12; 260/501.19; 260/501.21; 424/DIG. 4; 424/319
[58] Field of Search ........................ 260/501.12, 501.21, 260/501.19; 424/316, DIG. 4

[56] References Cited

FOREIGN PATENT DOCUMENTS 1085513  7/1954  France ........................... 260/501.12

*Primary Examiner*—James O. Thomas, Jr.
*Assistant Examiner*—Vera C. Clarke
*Attorney, Agent, or Firm*—Cushman, Darby & Cushman

[57] ABSTRACT

The invention is directed to compositions which can be orally administered to humans suffering from a condition characterized by excessive secretion of sebum from the scalp or skin, for the purpose of improving that condition. The compositions include a solid ingestible carrier admixed with certain non-toxic active compounds of the formula

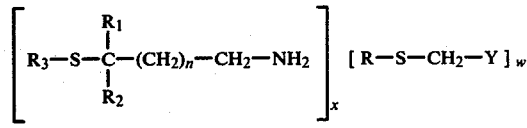

which are more fully and specifically described below.

6 Claims, No Drawings

ORALLY ADMINISTERED COMPOSITION CONTAINING ORGANIC AMINE-ORGANIC ACID ADDITION SALT FOR REDUCING EXCESSIVE SECRETION OF SEBUM ON HUMAN SKIN AND SCALP

CROSS REFERENCE TO RELATED APPLICATIONS

This is a division of Ser. No. 534,804 filed Dec. 20, 1974 (now U.S. Pat. No. 4,002,671); said Ser. No. 534,804 is in turn a division of Ser. No. 203,038, filed Nov. 29, 1971 (now U.S. Pat. No. 3,879,560). Ser. No. 203,038 is in turn a continuation-in-part of Ser. No. 801,840 filed Feb. 24, 1969 (now abandoned); of Ser. No. 858,161, filed Sept. 15, 1969 (now U.S. Pat. No. 3,671,643); of Ser. No. 12,122 filed Feb. 17, 1970 (now abandoned); and of Ser. No. 36,405 filed May 11, 1970 (now abandoned). Said Ser. No. 858,161 is in turn a continuation-in-part of Ser. No. 736,960, filed June 14, 1968 (now abandoned); of Ser. No. 801,840, filed Feb. 24, 1969 (now abandoned); and of Ser. No. 817,193, filed Apr. 17, 1969 (now abandoned). Said Ser. No. 736,960 is in turn a continuation-in-part of Ser. No. 427,976 filed Jan. 25, 1965 (now abandoned) and of Ser. No. 602,480 filed Dec. 19, 1966 (now abandoned).

This invention relates to compounds usefully employed in compositions which, when administered orally or topically to a human being having a scalp or skin charactericed by an excessive secretion of sebum, improves the condition of the scalp or skin by reducing said excessive secretion. The compounds of this invention are water-soluble salts and have the following formula

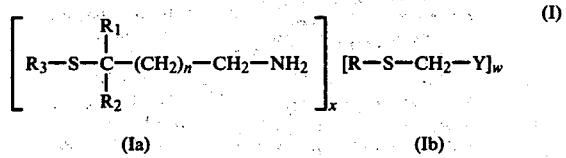

wherein n is 0 or 1 and when n is 0, $R_1$ and $R_2$ are selected from the group consisting of hydrogen and $CH_3$ and when n is 1, $R_1$ and $R_2$ are hydrogen; $R_3$ is selected from the group consisting of $R'_3$ and $R''_3$, $R'_3$ is selected from the group consisting of linear or branched alkyl having 1–18 carbon atoms, alkenyl having 3–18 carbon atoms, propyne-2 yl, mono or dihydroxy alkyl containing 2–4 carbon atoms, 1-2 dichloro-vinyl, $—C(C_6H_5)_3$, $—CO NH_2$, $—CH(C_6H_5)_2$, $—CH(C_6H_4p—OCH_3)_2$, $—C(CH_3)_2(C_6H_4p—OCH_3)$,

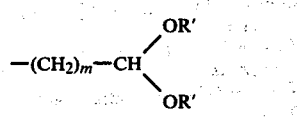

wherein R' is alkyl having 1–4 carbon atoms and m is 1–2,

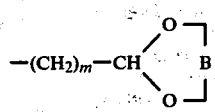

wherein m is 1–2 and B is selected from the group consisting of $$—CH_2—CH_2— \text{ and } —CH—CH_2—,$$
$$\qquad\qquad\qquad\qquad\qquad |$$
$$\qquad\qquad\qquad\qquad\quad CH_3$$

$—(CH_2)_z—R_9$ wherein z is 0, 1 or 2 and when z is 0, $R_9$ is selected from the group consisting of naphthyl-1, naphthyl-2, pyridyl-2, pyridyl-2 substituted with a member selected from the group consisting of nitro and alkyl having 1–4 carbon atoms, and pyridyl-2 N-oxide and when z is 1, $R_9$ is selected from the group consisting of naphthyl-1, naphthyl-2, thienyl-2, tetrahydrofuryl-2, furyl-2, pyridyl-2, pyridyl-2 substituted with a member selected from the group consisting of nitro and alkyl having 1–4 carbon atoms and pyridyl-2 N-oxide and when z is 2, $R_9$ is selected from the group consisting of pyridyl-2, pyridyl-2 substituted with a member selected from the group consisting of nitro and alkyl having 1–4 carbon atoms and pyridyl-2 N-oxide,

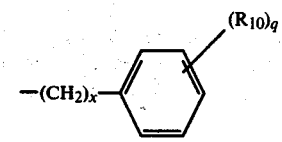

wherein x is 0–2 and wherein when q is 1, 2 or 3, $R_{10}$ is selected from the group consisting of hydrogen, halogen such as chlorine or bromine, alkoxy having 1–5 carbon atoms, linear or branched alkyl having 1–4 carbon atoms and when q is 1, $R_{10}$ is selected from the group consisting of acetamido, amino, phenoxy, cyclohexyl, methylenedioxy, trifluoromethyl, nitro, phenyl, dialkylamino, alkylthio, alkylsulfinyl and alkylsulfonyl wherein each alkyl moiety has 1–5 carbon atoms,

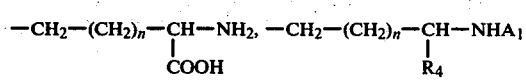

wherein n is 0 or 1, $R_4$ is selected from the group consisting of hydrogen and $COR_5$ wherein $R_5$ is selected from the group consisting of alkoxy having 1–5 carbon atoms, glucosamino, $—NH—NH_2$,

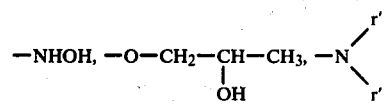

wherein r' is selected from the group consisting of hydrogen and alkyl having 1–3 carbon atoms,

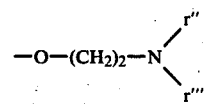

wherein r'' and r''' each independently represent alkyl having 1–3 carbon atoms or together with the nitrogen atom to which they are attached form a ring selected from the group consisting of morpholine, piperidine, pyrrolidine and N'-methylpiperazine, and $A_1$ is selected from the group consisting of $A'_1$ and hydrogen, $A'_1$ being selected from the group consisting of $—CONH_2$, nicotinoyl, glutamyl, $—COR_6$ and $SO_2R_7$ wherein $R_6$ is selected from the group consisting of hydrogen, alkyl having 1–18 carbon atoms, alkenyl having 2–18 carbon atoms,

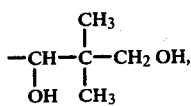

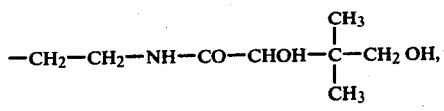

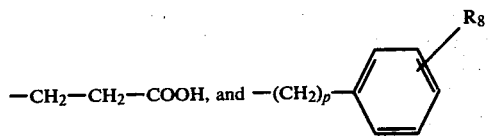

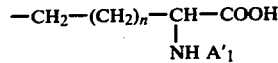

wherein $A'_1$ and n have have the meanings given above, and

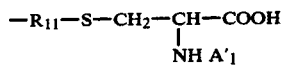

wherein $A'_1$ and $R_{11}$ have the meanings given above, and x is 1 or 2 and w is 1 or 2.

Representative of such active compounds which can be utilized in the compositions of this invention are set forth in Table I, below:

wherein p is 0–1 and $R_8$ is selected from the group consisting of hydrogen, alkyl having 1–4 carbon atoms, alkoxy having 1–4 carbon atoms, halogen and acetamido and wherein $R_7$ is selected from the group consisting of alkyl having 1–4 carbon atoms and

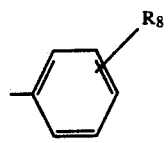

wherein $R_8$ has the meaning given below; $R''_3$ has the formula:

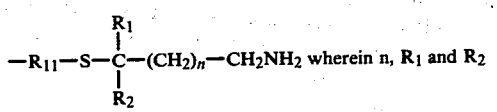

have the same meaning as above given and $R_{11}$ is selected from the group consisting of alkylene having 2–4 carbon atoms, alkylene having 2–4 carbon atoms and substituted with 1–2 hydroxy groups, butylene and —(CH$_2$)$_2$—SO$_2$—(CH$_2$)$_2$—; Y is selected from the group consisting of (a)

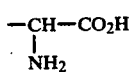

in which case R represents —(CH$_2$)$_s$—COOH wherein s is 1–5 and (b)

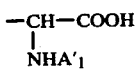

wherein $A'_1$ has the same meaning given above and R is selected from the group consisting of $R'_3$ except that in the value of $R'_3$ as

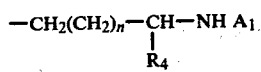

$A_1$ is other than hydrogen, —(CH$_2$)$_s$—COOH wherein s is 1–5,

Table I

| Active Compound Number | |
|---|---|
| 1. | 5-amino 3-thia hexanedioate of 2-benzylthio-ethylammonium, |
| 2. | 5-acetamido-3-thia-hexanedioate of di (2-benzyl-thio-ethylammonium), |
| 3. | 5-amino-3-thia hexanedioate of 2-(3-alanylthio) ethylammonium, |
| 4. | 5-amino 3-thia hexanedioate of 2-methylthio-ethylammonium, |
| 5. | 5-amino 3-thia hexanedioate of 3-benzylthio-propylammonium, |
| 6. | 2-amino 4-thia heptanedioate of 2-benzyl-thio-ethylammonium, |
| 7. | 5-amino 3-thia hexanedioate of 2-(2,2-dimethoxy-ethylthio)-ethylammonium, |
| 8. | 2-acetamido-3-benzylthio-propionate of 2-methyl-thioethylammonium, |
| 9. | 5-benzamido-3-thia-hexanedioate of di-(2-benzyl-thio-ethylammonium, |
| 10. | 5-nicotinamido-3-thia-hexanedioate of di (2-benzyl-thio-ethylammonium), |
| 11. | 5-p-toluenesulfonamido-3-thia-hexanedioate of di-(2-benzylthioethylammonium), |
| 12. | 5-p-acetamidobenzenesulfonamido-3-thia-hexanedioate of di- (2-benzylthioethylammonium), |
| 13. | 5-p-acetamidobenzamido-3-thia-hexanadioate of di-(2-benzylthioethylammonium), |
| 14. | 2-acetamido-4-thia-heptanedioate of di-(2-methyl-thio-ethylammonium), |
| 15. | 2-amino 4-thia decanedioate of 2-benzylthio-ethyl-ammonium, |
| 16. | 5-amino 3-thia hexanedioate of 2-benzylthiopropyl-ammonium, |
| 17. | 5-amino 3-thia hexanedioate of 2-benzylthio-2-methylpropylammonium, |
| 18. | 5-amino 3-thia hexanedioate of 2-phenylthio-ethyl-ammonium, |
| 19. | 5-amino 3-thia hexanedioate of 2-t-butylthioethyl-ammonium, |
| 20. | 5-amino 3-thia hexanedioate of 2-tritylthioethyl-ammonium, |
| 21. | 5-amino 3-thia hexanedioate of 2-thenylthioethyl-ammonium, |
| 22. | 5-amino 3-thia hexanedioate of 2-(2-pyridylmethyl-thio)ethylammonium, |
| 23. | 5-amino-3-thia hexanedioate of 2-(2-pyridylthio N-oxide)ethylammonium, |
| 24. | 5-amino 3-thia hexanedioate of 2-(2-butenylthio) ethylammonium, |
| 25. | 5-amino 3-thia hexanedioate of 2-(2-hydroxyethylthio) ethylammonium, |
| 26. | 5-amino 3-thia hexanedioate of 2-(2,3-dihydroxypropyl thio) ethylammonium, |
| 27. | 3-benzylthio 2-phenylacetamido propionate of 2-methyl-thioethylammonium, |
| 28. | 2-acetamido 3-tritylthiopropionate of 2-methylthio-ethylammonium, |
| 29. | 2-acetamido 3-benzhydrylthio propionate of 2-methyl- |

Table I-continued

| Active Compound Number | |
|---|---|
| | thioethylammonium, |
| 30. | 5-amino 3-thia hexanedioate of 6-methanesulfonamido-6-ethoxy carbonyl-4-thia hexylammonium, |
| 31. | 2-acetamido-4-thia-nonanedioate of 2,2'-thio bis (ethylammonium), |
| 32. | di-(β-benzylthioethylammonium)5-p-acetamido-3-thia-hexanedioate, |
| 33. | 5-amino-3-thia acid hexanedioate of 2-octadecylthio ethylammonium, |
| 34. | 2-amino-4-thia heptanedioate of 2-undecenylthio ethylammonium, |
| 35. | 2-amino-4-thia nonanedioate of 2-(3-hydroxypropylthio) ethylammonium, |
| 36. | di-(5-amino 3-thia hexanedioate) of 3-thia 1,6-hexanediammonium, |
| 37. | 2-amino-4-thia octanedioate of 2-(β-ureido ethylthio)-ethylammonium, |
| 38. | 5-amino-3-thia hexanedioate of 2-(3-methanesulfonamido propylthio) ethylammonium, |
| 39. | 2-amino-4-thia decanedioate of 2-thenylthio ethyl-ammonium, |
| 40. | 5-amino-3-thia hexanedioate of 2-(p-phenylbenzylthio) ethylammonium, |
| 41. | 5-tetradecanamido-3-thia hexanedioate of d-(2-β-hydroxyethyl thio ethylammonium), |
| 42. | 2-crotonamido-4-thia heptanedioate of di(2-tertio-butylthio ethylammonium), |
| 43. | 5-m-chlorobenzamido 3-thia hexanedioate of di-[2-(5-nitro 2-pyridyl) ethylammonium], |
| 44. | 2-butanesulfonamido 4-thia octanedioate of 2,2'-(2,3-dihydroxy 1,4-butanediyl dithio) diethylammonium, |
| 45. | 2-formamido 3-(propyn-2-ylthio) propionate of 3-(1-naphtyl thio) propylammonium, |
| 46. | 3-methylthio 2-trifluoroacetamido propionate of 2-oleylthio ethylammonium, |
| 47. | di-[3-(2,2 ethylenedioxy ethylthio) 2-ureido propionate] of 2,2'-thio diethylammonium, |
| 48. | 3-benzylthio 2-glutamino propionate of 2-tetra-hydrofurfurylthio ethylammonium, |
| 49. | 2-o-chlorobenzylthiomethyl 3-aza 4-oxo heptane-dioate of 5,5'-sulfonyl bis(3-thia pentylammonium), |
| 50. | 2-acetamido 3-p-methylthiophenylthio propionate of 2-(2,4,6-trimethyl benzylthio) ethylammonium, |
| 51. | 3-(3,4-methylenedioxy benzylthio) 2-propionamido propionate of 3-[2-(2,4-dihydroxy, 3,3-dimethyl butyramido) ethylthio]propylammonium, |
| 52. | 5-amino 3-thia hexanedioate of 2-(3,4-dichlorobenzyl-thio) ethylammonium, |
| 53. | 2-butyramido 3-isopropylthio propionate of 2-(2,6-dichloro benzylthio) ethylammonium, |
| 54. | 2-acetamido 3-(3-alanylthio) propionate of 2-m-fluorobenzylthio ethylammonium, |
| 55. | 6-amino 3-thia heptanedioate of 2-p-dimethylamino-benzylthio ethylammonium, |
| 56. | 2-benzenesulfonamido 3-furfurylthio propionate of 2-(2,4-dichloro phenylthio) ethylammonium, |
| 57. | 2-hexanamido di-(p-methoxyphenyl) 3-methylthio pro-pionate of 2-(2,3-dihydroxy propylthio)ethylammonium, |
| 58. | 5-amino 3-thia hexanedioate of 2-(6-methyl 2-pyridylthio) propylammonium, |
| 59. | 5-amino 3-thia hexanedioate of 2-(o-chlorobenzylthio) ethylammonium, |
| 60. | 5-amino 3-thia hexanedioate of 2-(p-bromobenzylthio) ethylammonium, |
| 61. | 5-acetamido 3-thia hexanedioate of di-2-(2,4-dichlo-robenzylthio) ethylammonium, |
| 62. | 2-acetamido-3-p-fluorobenzylthio propionate of 2-hexadecylthio ethylammonium. |

I. Preparation of Active Compounds

The active compounds having formula (I) can be prepared under atmospheric pressure by dissolving or suspending one of the corresponding acid (Ia) or basic (Ib) reactants in a solvent therefor and then adding progressively the other of said reactants, while stirring. The resulting mixture can be heated to reflux. Thereafter, the reaction mixture is left to stand for several hours at a temperature ranging between about −20° to +5° C. Under these conditions, the desired salt precipitates or crystallizes and can be removed by conventional separation procedures such as by filtration. Generally the basic reactant (Ib), is used in stoichiometric proportions, or slightly in excess of stoichiometry relative to the acid reactant (Ia). The acid and basic reactants can, if desired, be prepared in a manner essentially as outlined in Ser. No. 140,956 filed May 6, 1971, now U.S. Pat. No. 3,821,405.

The following examples illustrate the preparation of the active compounds of the present invention:

EXAMPLE 1

Preparation of 5-amino 3-thia hexanedioate of 2-benzylthio-ethylammonium having the formula:

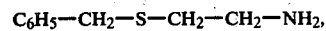
$C_6H_5-CH_2-S-CH_2-CH_2-NH_2$,

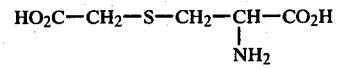
$$HO_2C-CH_2-S-CH_2-\underset{\underset{NH_2}{|}}{CH}-CO_2H$$

16.7 g of 2-benzylthio ethylamine are introduced in a 250 cm³ flask equipped with a reflux condenser and containing a suspension of 17.9 g of S-carboxy-methyl-l-cysteine in 95 cm³ of tetrahydrofuran, while the mixture is being agitated.

The mixture is heated to the boiling point of the solvent and water is then added drop by drop until a vigorous exothermic reaction is initiated, which is followed by the formation of solids in the reaction mixture. This is left to stand overnight at −10° C.

After filtration, the precipitate is rinsed in tetrahydrofuran, then in acetone, drained and vacuum dried at 50° C.

The result is 31.2 g of 5-amino 3-thia hexanedioate of 2-benzylthio-ethylammonium.

This compound melts at 146°–148° C.

Analysis reveals that it contains 18.5% by weight of sulfur, the theoretical percentage of sulfur being 18.55%.

The resulting compound is insoluble in alcohols and conventional organic solvents even when hot. On the other hand, it is very soluble in water and in an aqueous lower alkanol medium.

EXAMPLE 2

Preparation of 5-acetamido-3-thia-hexanedioate of di (2-benzylthio-ethylammonium) having the formula:

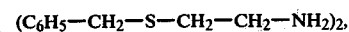
$(C_6H_5-CH_2-S-CH_2-CH_2-NH_2)_2$,

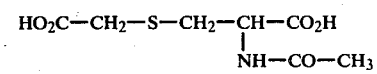
$$HO_2C-CH_2-S-CH_2-\underset{\underset{NH-CO-CH_3}{|}}{CH}-CO_2H$$

0.1 mol of 2-benzylthio ethylamine is added drop by drop to a conical 100 cm³ flask containing 0.05 mol of 5-acetamido-3-thia-hexanedioic acid in solution in 30 cm³ of absolute ethanol. The reaction mixture is then left to stand overnight at −15° C.

5-acetamido 3-thia-hexanedioate of di (2-benzylthio ethylammonium) crystallizes out in the form of fine needles, which are filtered out, washed in absolute ethyl alcohol, and vacuum dried in the presence of phosphoric anhydride.

The yield of the reaction is 65%.

The resulting product is in the form of white needles having a melting point of 120° C.

It is insoluble in ethanol, but very soluble in water and in a mixture of water and ethyl alcohol.

EXAMPLE 3

Preparation of 5-amino 3-thia hexanedioate of 2-(3-alanylthio) ethylammonium responding to the formula:

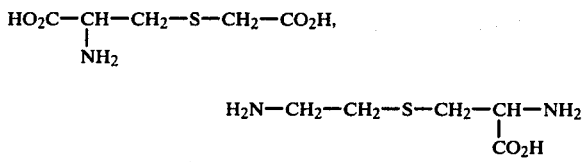

16.4 g of 3-(2-aminoethylthio) alanine are dissolved in a mixture of 250 cc of methanol and 50 cc of water. Into this solution, vigorously agitated and heated to reflux there are added 17.9 g of S-carboxy-methyl-cysteine, little by little. The salt precipitates, and the precipitate is filtered, washed with absolute methanol, and dried. The yield is 85%.

The resulting compound is a white solid melting at 186° C. It is soluble in water but insoluble in alcohols.

EXAMPLE 4

Preparation of 5-amino 3-thia hexanedioate of 2-methylthio-ethylammonium having the formula:

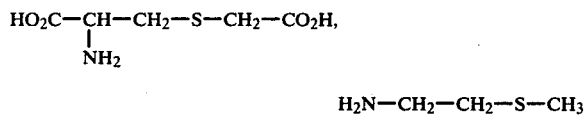

In the same manner as in Example 3, 9 g of S-carboxy-methyl-cysteine are reacted with 5 g of 2-methylthio-ethylamine. This reaction is carried out in ethanol.

The resulting product is a white solid melting at 205°–210° C.

It is soluble in water, insoluble in ethanol and in other ordinary solvents but soluble in hot methanol.

EXAMPLE 5

Preparation of 5-amino 3-thio hexanedioate of 3-benzylthiopropylammonium having the formula:

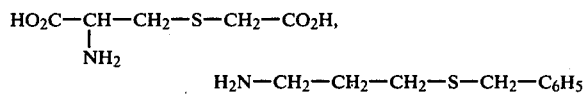

In the same manner as in Example 1, 8.9 g of S-carboxymethyl cysteine are reacted with 9.1 g of 3-benzylthio-propylamine in ethanol.

The result is 16.5 g of a white solid melting at 129° C. It is soluble in water and, when hot, in ethanol.

EXAMPLE 6

Preparation of 2-amino 4-thia heptanedioate of 2-benzylthio-ethylammonium having the formula:

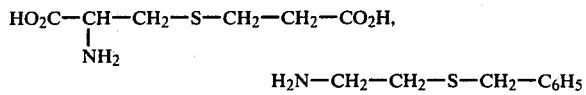

In the same manner as in Example 1, 38.6 g of S-carboxyethyl cysteine are reacted with 33.4 g of 2-benzylthio-ethylamine in ethanol.

The result is 60.5 g of a white solid melting at 95° C., soluble in water and insoluble in alcohols.

EXAMPLE 7

Preparation of 5-amino 3-thia hexanedioate of 2-(2,2-dimethoxy-ethylthio)-ethylammonium, having the formula:

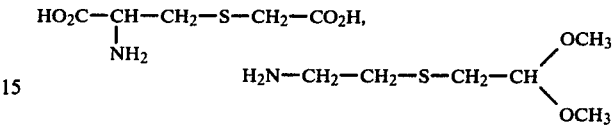

In the same manner as in Example 3, 17.9 g of S-carboxy methylcysteine are reacted with 18 g of 2-(2,2-dimethoxyethylthio)-ethylamine, in absolute methanol at room temperature.

The result is 24 g of a white hygroscopic solid which melts between 130° and 140° C., is soluble in water, insoluble in ethanol and in ordinary solvents, but slightly soluble in methanol.

EXAMPLE 8

Preparation of 2-acetamido 3-benzylthiopropionate of 2-methylthioethylammonium having the formula:

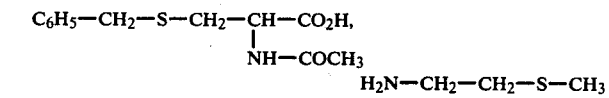

In the same manner as in Example 2, 25.3 g of N-acetyl S-benzyl l-cysteine are reacted with 9.1 g of 2-methylthio-ethylamine in ethanol.

The result is 24 g of a product in the form of white needles, which melts at 131° C. and is soluble in water and alcohol.

Active compounds Nos. 9–65 listed above are prepared in a manner essentially as described in Example 2, employing corresponding amounts of the appropriate cysteamine derivative for the 2-benzylthio ethylamine and of the appropriate cysteine derivative for the 5-acetamido 3 thia hexanedioic acid of Example 2.

The compounds of the present invention can advantageously be incorporated into both topically applied and orally administered compositions for use by persons having a scalp or skin characterized by an excessive secretion of sebum to reduce or diminish said excessive secretion.

II. Topically Applied Compositions

In accordance with the present invention, there is provided a variety of compositions which can be topically applied to the scalp or skin to achieve the aforementioned result and these compositions can include dermal preparations which can be in the form, for instance, of a cream, milk, lotion, gel, cake or aerosol. The active ingredient of this invention is present in these topically applied compositions in amounts of about 0.1–5 percent, preferably about 0.75–3 percent, by weight of the total composition. Generally, these compositions have a pH ranging from about 3 to 13 and are solutions of the active ingredient in water, a lower alkanol or aqueous solutions of a lower alkanol wherein the lower alkanol is present in amounts of about 20 to 70 weight percent of said aqueous solutions. The choice of solvent for the active ingredient can depend on a number of easily ascertainable factors such as the particular active ingredient chosen, its solubility characteristics, the ultimate use of the composition and the like. When a lower alkanol, alone or as an aqueous solution thereof, is selected, generally the alkanol is ethanol or isopropanol. In addition to the solvent, the active ingredient-containing composition can also be formulated with conventional adjuvants such as emulsifiers, preservatives, perfumes, dyes, emollients, waxes, pigments, detergents—cationic, anionic, nonionic and amphoteric, thickeners, oils and the like.

When the topically applied compositions of the present invention are employed in aerosol form, generally the active ingredient is present as a solution thereof in a lower alkanol, together with a conventional aerosol propellant such as a fluorinated hydrocarbon such as dichlorodifluoromethane, trichloromonofluoromethane and mixtures thereof. Obviously, other well-known propellants can also be used. Generally, the propellant is present in amounts of about 66 to 75 weight percent of the total aerosol composition, which is, of course, packaged under pressure.

The topically applied compositions also include hair setting lotion and lacquer formulations. Again, the active compound of this invention is present in such formulations in amounts ranging from about 0.1-5 percent by weight of said formulation, and is present as a solution thereof in water, lower alkanol or mixtures thereof as defined above. Additionally such hair setting lotions and lacquers also include, advantageously, a film-forming resin having a molecular weight ranging from about 10,000 to 3,000,000. Typical film forming resins include polyvinyl pyrrolidone having a molecular weight of about 10,000-700,000; copolymers of vinyl pyrrolidone and vinyl acetate wherein the ratio of VP to VA can range between 70:30 to 30:70 and which have a K value (1% ethanol solution) of about 20-50;copolymers of vinyl acetate, crotonic acid and an acrylic or methacrylic ester; copolymers of vinyl acetate and a vinyl alkyl ether; copolymers of vinyl acetate, crotonic acid and a vinyl ester of a long carbon-chain acid or an allyl or methallyl ester of a long carbon-chain acid; copolymers of an ester of an unsaturated alcohol and a short chain carboxylic acid, a short carbon-chain unsaturated acid at least one ester derived from a short chain saturated alcohol and an unsaturated acid; and copolymers of at least one unsaturated ester and at least one unsaturated acid. A specific vinyl acetate/crotonic acid copolymer usefully employed is that sold under the trade name RESYN 28.1310 having a molecular weight of 20,000. Other resins usefully employed are those sold under the trade name GANTREZ including GANTREZ AN 3953 which is the half butyl ester of GANTREZ AN 119 which is methylvinylether/maleic anhydride copolymer having a specific viscosity of 0.1-0.5 in a 1% solution of the copolymer in methylethyl ketone at 25° C.

The hair setting and lacquer formulations can also be packaged in aerosol form using the aerosol propellants and the amounts thereof as described above.

Yet another topically applied composition according to the invention is a shampoo formulation which also contains the active ingredient in amounts of about 0.1-5 percent by weight. Again, the carrier for said active compound can be water or an aqueous solution of a lower alkanol as described above. In addition, these shampoo compositions which have a pH of about 3-8 also contain about 5-60% of an anionic, amphoteric, cationic or nonionic detergent.

Anionic detergents include both the soap and non-soap detergents. Examples of suitable soaps are the sodium, potassium, ammonium and alkanol ammonium salts of higher fatty acids ($C_8$–$C_{20}$). Examples of anionic non-soap detergents are alkyl glyceryl ether sulfonates, alkyl sulfates, alkyl ether sulfates, alkyl sulfonates, alkyl monoglyceride sulfates or sulfonates, alkyl polyethoxy ether sulfates, alkanolamide sulfonates, alkanolamide sulfates, alkyl monosulfosuccinates, acyl sarcosinates, acyl esters of isethionates, acyl-N-methyl taurines, alkyl benzene sulfonates and alkyl phenol polyethoxy sulfonates. In these compounds the alkyl and acyl moieties, respectively, can contain 8-20 carbon atoms and they can be used in the form of water-soluble salts such as the sodium, potassium, ammonium and alkanol ammonium salts.

Suitable examples of cationic detergents are dilauryldimethyl ammonium chloride, diisobutyl phenoxy ethoxy ethyl dimethylbenzyl ammonium chloride, cetyl trimethyl ammonium bromide, N-cetyl pyridinium bromide and benzethonium chloride, lauryl benzyl trimethyl ammonium bromide or chloride, myristyl benzyl trimethyl ammonium bromide or chloride and cetyl benzyl trimethyl ammonium bromide or chloride.

Suitable examples of amphoteric detergents are aspargine derivatives, alkyl dimethyl betaine, alkyl betaamino propionates wherein the alkyl moiety contains 10-20 carbon atoms, basic quaternary ammonium compounds derived from 2-alkyl-substituted imidazoline and compounds having the formula

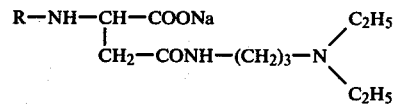

wherein R is a radical derived from fatty acids of copra and radicals ($C_8$ to $C_{20}$) derived from tallow.

Representative nonionic detergents are ethylene oxide adducts of fatty alcohols, long chain phenols (e.g. octadecyl phenol), long chain mercaptans or long chain amides, such as lauryl alcohol oxyethylenated with 12 moles ethylene oxide and $C_{12}$ thiols oxyethylenated with 12 moles of ethylene oxide.

The shampoo formulations can, of course, contain any of the usual shampoo additives such as color, perfume, thickeners, solvents, opacifiers, suds builders, conditioning agents, preservatives, buffers and antistatic agents. Generally 10-20 $cm^3$ of the shampoo composition applied to the scalp and hair once a week for about 4 weeks provides desirable results.

Still further topically applied compositions according to the present invention include hair dye compositions for coloring human hair. These compositions contain the active compound of this invention in the aforesaid quantities and in an aqueous or aqueous alkanol solution as described above. Conventional hair dyes, such as azo, anthraquinone and nitro dyes of the benzene series can be used in such compositions in amounts sufficient to color the hair. Representative dyes include parapheylene diamine, 2,5-toluene diamine sulfate, chloroparaphenylene diamine sulfate, nitroparaphenylene diamine, 1,2,4-triamino benzene dihydrochloride, paraaminodiphenyl amine, ortho phenylene diamine, 4-chloro ortho phenylene diamine, 4-nitro ortho phenylene diamine, paraaminophenol, 4-amino-2-methyl phenol sulfate, 4-amino-3-methyl phenol, 4-amino-2-nitro phenol, 2,4-diaminophenol hydrochloride, paramethyl amino phenol sulfate, ortho aminophenol, 4-chloro-2-aminophenol, 4-nitro-2-aminophenol, 5-nitro-2-aminophenol, 4,6-dinitro-2-aminophenol, 6-chloro-4-nitro-2-aminophenol hydrochloride, 4-amino diphenylamine, 4,4′-diamino diphenylamine sulfate, meta phenylene diamine, chlorometa phenylene diamine, nitro-meta phenylene diamine, meta toluylene diamine, 2,4-diamino anisol sulfate, meta amino phenol, 3,5-diamino phenol hydrochloride, diethyl meta aminophenol, paraamino ortho cresol, 1-hydroxy-2,4-di-(p-trimethylammoniumphenylamino)anthraquinone methosulfate, 1-hydroxy-2,4-di(p-trimethylammonium phenylamino) anthraquinone iodide, 1-aminopropylamino anthraquinone, and N-γ-amino propylamino-4, N′-methylamino-1 anthraquinone. Additional examples of commercially available useful dyes include, as monoazo dyes, CI Acid Blue 92 (13390), CI Acid Yellow 23 (19140); as diazo dyes, CI Acid Orange 24 (20170); as triphenylmethane type dyes, CI Acid Blue 1 (42045), CI Acid Violet 19 (42685), CI Acid Blue 22 (42755), CI Acid Violet 15 (43525); as xanthene dyes, CI Acid Violet 9 (45190); as azine dyes, CI Acid Black 2 (50420), CI Acid Blue 59 (50315), CI Acid Blue 61 (50330); as anthraquinone dyes, CI Acid Violet 43 (60730), CI Acid Blue 80 (61585), CI Acid Violet 51 (62165), CI Acid Blue 138 (62075); as premetallized dyes, both 1:1 and 2:1 complexes-chromium and cobalt, for instance, CI Acid Black 43 (15691); as disperse dyes, CI Disperse Blue 14 (61500), CI Disperse Blue 6 (62050), CI Disperse Blue 31 (64505); as direct dyes, CI Direct Blue 2 (22590), CI Direct Black 51 (27720), CI Direct Violet 51 (27905); and as solvent dyes, 15680 and CI Solvent Violet 10 (45190).

Yet another topically applied composition including the active compounds of the present invention is a formulation for use in effecting a permanent wave or deformation of oily hair.

In one embodiment of the use of such permanent wave formulations, the hair is permanently waved by applying to the hair wound on curlers during the first stage, i.e., during the reducing stage, a cosmetic composition comprising a mixture of a reducing agent and the active compound of this invention as defined above, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, an oxidizing or neutralizing agent to reform the disulphide bonds of the keratin of the hair.

In another embodiment of using these permanent wave formulations the hair is permanently waved by applying to the hair wound on curlers during the first stage, i.e., during the reducing stage, a reducing agent, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, a cosmetic composition comprising a mixture of an oxidizing or neutralizing agent and the active compound as defined hereinbefore whereby the disulphide bonds of the keratin of the hair are reformed.

In an alternative procedure the hair is permanently waved by impregnating the hair wound on curlers with a cosmetic composition comprising a mixture of a thiol reducing agent for altering the disulphide bonds of the keratin of the hair, an organic disulphide and the active compound of the present invention, the molar ratio of said organic disulphide to said thiol being greater than 1, and as high as about 20, permitting the composition to remain on the hair for a time sufficient to induce a permanent wave therein, generally about 10 to 40 minutes, and unwinding the hair from the curlers. Conventional separate neutralization operations are not required in the practice of this embodiment of the invention.

The active compound of this invention used in these permanent wave formulations is admixed with a conventional reducing agent and is present in the resulting mixture in amounts between 0.1 to 5% by weight of the total and preferably between 1 and 3 weight percent. The pH of this cosmetic composition is preferably between 3 and 9.5. Conventional reducing agents employed are advantageously those organic thiols which are generally used to perform the first stage of a permanent waving operation. Representative thiols include thioglycolic acid, ammonium thioglycolate, thioglycerol, thiolactic acid, thioglycolic amide or hydrazide or the like.

Conveniently, and also in accordance with the present invention, the reducing composition is a two-package composition, the first package containing a thiol reducing agent as described above and the second package containing the active compound of this invention in amounts such that when the contents of two packages are mixed together, preferably just before initiation of the reducing operation, the resulting reducing composition contains said active compound in amounts of about 0.1–5 weight percent of the total mixture.

Alternatively, the said active compound is admixed with a conventional neutralizing or oxidizing agent and is present in the resulting mixture in amounts between 0.1 to 5 weight percent, and preferably between about 1 and 3 weight percent of the total. Conventional neutralizing agents employed include, for instance, hydrogen peroxide, sodium or potassium bromate, sodium perborate or percarbonate and the like.

Conveniently also, the neutralizing composition is a two-package composition, the first package containing the neutralizing agent as described above and the second package containing said active compound also as defined above in amounts such that when the contents of the two packages are mixed together, preferably just before initiation of the neutralizing operation, the resulting neutralizing composition contains the active compound in amounts of about 0.1–5 weight percent of the total mixture.

As a further alternative, the active compound is admixed with a single stage permanent hair waving agent, and is present in the resulting mixture in amounts between 0.1–5 weight percent, and preferably, between about 1 and 3 weight percent of the total. Conventional single stage permanent hair waving agents can be employed and include a mixture of an organic disulfide and a thiol, the mol ratio of the disulfide to the thiol being greater than 1.

Suitable thiols include thioglycolic acid, glycol thioglycolate, glycerol thioglycolate, β-mercaptoethanol, N-carboxymethyl-mercaptoacetamide, glycol thiolactate and the like.

As the organic disulphides there can be used the disulphides of the thiols set forth in the preceding paragraph. For instance, glycol dithiodiglycolate, glycerol dithioglycolate, glycol dithiodilactate, dithiodiethanol and N-carboxymethyldithioacetamide can be employed. Additional ingredients can include ammonia, water, urea and lower alkanols in conventionally employed amounts and the pH of the single stage permanent hair waving agent ranges between about 8–10, preferably about 8.5–9.5. Typical formulations of such single stage permanent hair waving agents are disclosed in French Pat. Nos. 1,443,888 and 1,455,788.

Again, conveniently, the single stage permanent hair waving composition is a two-package composition, the first package containing the single stage permanent hair waving agent and the second package containing the active compound, as defined above, in amounts such that when the contents of the two packages are mixed together, preferably just before use, the resulting permanent hair waving composition contains the active compounds in amounts of about 0.1–5 weight percent of the total mixture.

As will be recognized, these permanent wave formulations can also include other additives conventionally employed such as penetrating agents, surfactants, dyes or perfumes and can be admixed with conventional vehicles such as water, lower alkanols and their mixtures as defined above. Further, they can also be provided in the form of a solution, a foam, a cream or gel or can be provided in the form of a sprayable aerosol especially when the cosmetic vehicle is water, lower alkanol or their mixtures. The sprayable aerosol can include an amount of a liquefied gas under pressure, such as a fluorochlorinated hydrocarbon, also as defined hereinbefore.

In yet another embodiment of the present invention, a dermal lotion composition can be prepared which contains as the active ingredient the compound defined above present in amounts of about 0.1–3 percent by weight of said composition. Additionally, where the active compound comprises a free carboxylic acid group, this can take the form of a complex with a cationic quaternary ammonium bactericide, such as (diisobutylphenoxyethoxyethyl dimethyl benzyl) ammonium chloride monohydrate or (diisobutyl cresoxyethoxyethyl dimethyl benzyl) ammonium chloride monohydrate.

III. Orally Administered Compositions

In accordance with another embodiment of the present invention, there is provided a composition and method for treating a scalp characterized by an excessive secretion of sebum, to improve the condition thereof by reducing said excessive secretion which comprises orally administering to a human being having a scalp so characterized a therapeutic composition comprising an ingestible carrier admixed with, as a non-toxic active ingredient, an active compound as defined hereinabove.

These novel compositions can be in liquid or solid form and when the liquid form is desired, the active compound can be dissolved in an alimentary liquid, such as water or an aqueous solution of a non-toxic lower alcohol, such as ethanol. These liquid orally administered compositions generally contain about 1–1.5 percent by weight of the active compound, the remainder being essentially the ingestible carrier.

The orally administered compositions can also be provided as a solid, in the form of granules, pills, tablets and the like, and in this form the active compound is generally present in amounts of about 0.75–20 weight percent of the composition. Examples of suitable excipient or carrier formulations can be found in U.S. Pat. No. 2,888,380.

These compositions, whether in liquid or solid form, can be orally administered at a rate of about 1–5 mg/kg/day based on the weight of the human being, and they are generally administered during a period of about 15 days. After 15 days, the treatment may be stopped and then resumed 15 days later.

IV. Examples of Topically Applied Compositions

EXAMPLE 9

A shampoo having the following composition is prepared:

| | |
|---|---|
| Technical (100%) triethanolamine lauryl sulfate | 4 g |
| Lauryl diethanolamide | 2 g |
| 5-amino 3-thia hexanedioate of 2-benzyl-thioethylammonium | 1 g |
| Carboxymethylcellulose | 0.2 g |
| Perfume, phenilic alcohol, benzyl acetate, etc. | 0.3 g |
| Water, q.s.p. | 100 g |

EXAMPLE 10

A shampoo having the following composition is prepared:

| | |
|---|---|
| Technical (100%) alkyl sodium sulfate O E | 5 g |
| Pure mono lauryl sodium sulfosuccinate | 1 g |
| Polyethylene glycol distearate | 1.5 g |
| Lauryl diethanolamide | 2.5 g |
| 5-amino 3-thia hexanedioate of 2-benzylthioethylammonium | 2 g |
| Perfume, Patchoulis or rose extracts | 0.3 g |
| Lactic acid, q.s.p. pH = 6.5 | |
| Water, q.s.p. | 100 g |

EXAMPLE 11

A shampoo having the following composition is prepared:

| | |
|---|---|
| 100% alkyl sodium sulfate paste | 15 g |
| Condensation product of fatty acids of copra and methyltaurine, a paste sold under the trademark "Hostapon C.T." by the Hoechst Co. | 40 g |
| Lauryl monoethanolamide | 3 g |
| Glycerol monostearate | 2 g |
| 5-amino 3-thia hexanedioate of 2-benzylthioethylammonium | 1 g |
| Lactic acid, q.s.p. pH = 6.6 | |
| Perfume, phenilic alcohol or natural extracts | 0.4 g |
| Water, q.s.p. | 100 g |

EXAMPLE 12

A shampoo having the following composition is prepared:

| | |
|---|---|
| Alkyl sodium sulfate powder | 54 g |
| Product of the condensation of the fatty acids of copra with sodium isethionate sold under the trademark "Hostapon K.A." by the Hoechst Co. | 40 g |
| 5-amino 3-thia hexanedioate of 2-benzyl-thioethylammonium | 5 g |
| Perfume, like cinnamic alcohol or natural extracts | 1 g |

EXAMPLE 13

A shampoo according to the present invention is prepared as follows:

| | |
|---|---|
| Technical (100%) triethanolamine lauryl sulfate | 4 g |
| Lauryl diethanolamide | 2 g |
| 5-amino 3-thia hexanedioate of 2-(o-chlorobenzylthio) ethylammonium | 1 g |
| Carboxymethylcellulose | 0.2 g |
| Perfume, phenilic alcohol, benzyl acetate, etc. | 0.3 g |
| Water, q.s.p. | 100 g |

EXAMPLE 14

A shampoo having the following composition is prepared:

| | |
|---|---|
| Technical (100%) alkyl sodium sulfate O.E. | 5 g |
| Pure mono lauryl sodium sulfosuccinate | 1 g |
| Polyethylene glycol distearate | 1.5 g |
| Lauryl diethanolamide | 2.5 g |
| 5-amino 3-thia hexanedioate of 2-(p-bromobenzylthio) ethylammonium | 2 g |
| Perfume, Patchoulis or rose extracts, etc. | 0.3 g |
| Lactic acid, q.s.p. PH = 6.5 | |
| Water, q.s.p. | 100 g |

EXAMPLE 15

A shampoo having the following composition is prepared:

| | |
|---|---|
| 100% alkyl sodium sulfate paste | 15 g |
| Condensation product of fatty acids of copra and methyltaurine, a paste sold under the tradename "Hostapon C.T." | 40 g |
| Lauryl monoethanolamide | 3 g |
| 2-amino 4-thia heptanedioate of 2-benzylthioethylammonium | 1 g |
| Lactic acid, q.s.p. pH = 6.6 | |
| Perfume (phenilic alcohol or natural extracts) | 0.4 g |
| Water, q.s.p. | 100 g |

EXAMPLE 16

A shampoo having the following composition is prepared:

| | |
|---|---|
| Alkyl sodium sulfate powder | 54 g |
| Product of the condensation of the fatty acids of copra with sodium isethionate sold under the tradename "Hostapon K.A." | 40 g |
| 5-amino 3-thia hexanedioate of 3-benzylthiopropylammonium | 5 g |
| Perfume (cinnamic alcohol or natural extracts) | 1 g |

EXAMPLE 17

The following hair waving reducing composition is prepared:

| | |
|---|---|
| Ammonium thioglycolate | 9.5 g |
| Fatty alcohol polyethoxy-ester (Cetyl alcohol 30% - stearyl alcohol 70%) sold under the tradename "Sipol Wax AO" | 0.8 g |
| Ammonia solution, q.s.p. 0.7 N | |
| 5-amino 3-thia hexanedioate of 2-phenylthioethylammonium | 1 g |
| Water, q.s.p. | 100 g |

After shampooing and drying, the hair is wound on curlers and is impregnated with the above composition. The composition is allowed to act for 15 to 30 minutes. Thereafter, the hair is thoroughly rinsed and there is then applied to the hair a neutralizing composition comprising a 6-volume hydrogen peroxide solution. The curlers are removed and the hair is rinsed and dried. The hair thus permanently waved in accordance with this invention exhibited a non-oily appearance for a significantly longer time than did the hair when permanently waved using essentially the same cosmetic composition but without 5-amino 3-thia hexanedioate of 2-phenylthio-ethylammonium.

EXAMPLE 18

The first stage, i.e., the reducing stage, of a permanent waving operation is performed with a reducing composition containing:

| | |
|---|---|
| Ammonium thioglycolate | 9.5 g |
| (cetyl alcohol 30% - stearyl alcohol 70%) sold under the tradename of "Sipol Wax AO" | 0.8 g |
| Ammonia solution, q.s.p. 0.7 N | |
| Water, q.s.p. | 100 g |

A two-package neutralizing composition is then employed, the first package containing:

| | |
|---|---|
| Hydrogen peroxide, q.s.p. 6.6 volumes | |
| Citric acid | 0.1 g |
| Water, q.s.p. | 100 g |
| and the second package containing: | |
| 5-amino 3-thia hexanedioate of 3-benzylthiopropylammonium | 1 g |

Immediately prior to initiating the second stage of the permanent waving operation, i.e., the neutralizing stage, the powdered 5-amino 3-thia hexanedioate of 3-benzylthio-propylammonium is dissolved in the hydrogen peroxide solution and the hair previously treated with the above reducing agent, being soft and pliable and still wound on curlers, is treated with the resulting neutralizing solution for a time sufficient to reform the disulphide bonds in the keratin of the hair.

After the hair has been rinsed, unwound from the curlers, and dried, a permanent wave is obtained which exhibits good holding characteristics. Equally important, however, is that the hair remained non-oily in appearance for a significantly longer time than did the hair when permanently waved using essentially the same neutralizing composition but without compound of the invention.

EXAMPLE 19

A composition according to the invention is prepared by dissolving 1.5 g of 5-amino 3-thia hexanedioate of 2-(p-phenylbenzylthio) ethylammonium in 100 cc of perfumed distilled water.

EXAMPLE 20

A composition in accordance with the invention is obtained by dissolving 0.75 g of 5-amino 3-thia hexanedioate of 2-octadecylthio ethylammonium in 100 cc. of a 50% ethanolic aqueous solution.

EXAMPLE 21

A composition in accordance with the invention is prepared by dissolving 2 g of 2-hexaneamido di-(p-methoxyphenyl) 3-methyl thiopropionate of 2-(2,3-dihydroxypropylthio) ethylammonium in 100 cc of a 20% ethanolic aqueous solution.

EXAMPLE 22

A grooming lotion for gentlemen is prepared by mixing:

| | |
|---|---|
| 3-methylthio 2-trifluoroacetamido propionate of 2-oleylthio ethyl-ammonium | 0.75 g |
| Dimethylhydantoin formaldehyde resin | 0.5 g |
| Dimethyldilaurylammonium chloride | 0.5 g |
| Perfume | 0.1 g |
| Ethanol | 50 cc |
| Water, q.s.p. | 100 cc |

EXAMPLE 23

A grooming liquid gel is prepared by mixing:

| | |
|---|---|
| 3-benzylthio 2-glutamino propionate of 2-tetrahydrofurfurylthio ethylammonium | 0.1 g |
| Carboxyvinylpolymer-carboxypolymethylene, sold under the trade name "Carbopol 940" | 0.45 g |
| Polyvinylpyrrolidone (M.W. 40000) | 2 g |
| Lanolin oxyethylenated with 16 moles ethylene oxide | 1 g |
| Polyethyleneglycol (M.W. 300) | 5 g |
| Methylparahydroxybenzoate, sold under the trade name "Nipagin M" | 0.1 g |
| n-propyl-p-hydroxybenzoate, sold under the trade name "Nipasol" | 0.1 g |
| Perfume | 0.1 g |
| Triethanolamine, q.s.p. pH 8 | |
| Water, q.s.p. | 100 cc |

EXAMPLE 24

A cream for use on the face is prepared by mixing together:

| | |
|---|---|
| 2-o-chlorobenzylthiomethyl 3-aza 4-oxo heptanedioate of 5,5'-sulfonyl bis (3-thia pentylammonium) | 2 g |
| Cetyl-stearyl alcohol oxyethylenated with 15 moles ethylene oxide | 7 g |
| Silicone oil (dimethylpolysiloxane having a viscosity of 20°–22° at room temperature) | 1 g |
| Diethyleneglycolstearate | 6 g |
| Methylparahydroxybenzoate sold under the trade name "Nipagin M" | 0.10 g |
| n-propyl-p-hydroxybenzoate sold under the trade name "Nipasol" | 0.10 g |
| Water, q.s.p. | 100 cc |

EXAMPLE 25

A milk is prepared by mixing together:

| | |
|---|---|
| 2-benzenesulfonamido 3-furfurylthio propionate of 2-(2,4-dichlorophenyl-thio) ethylammonium | 3 g |
| Carboxyvinylpolymer-carboxypolymethylene, sold under the trade name "Carbopol 934" (U.S. Pat. 3,133,865) | 0.375 g |
| Isopropylester of fatty acids of lanolin | 1 g |
| Lanolin oxyethylenated with 16 moles ethylene oxide | 2.5 g |
| Cetyl-stearyl alcohol oxyethylenated with 15 moles ethylene oxide | 3 g |
| Substituted alkylamide | 2 g |
| Ethyl alcohol | 20 cc |
| Triethanolamine, q.s.p. pH 8 | |
| Methylparahydroxybenzoate, sold under the trade name "Nipagin M" | 0.10 g |
| n-propylparahydroxybenzoate, sold under the trade name "Nipasol" | 0.10 g |
| Water, q.s.p. | 100 g |

EXAMPLE 26

A masking cream is prepared by mixing the following ingredients:

| | |
|---|---|
| 2-acetamido 3-(3 alanylthio)-propionate of 2-m-fluorobenzylthio ethylammonium | 5 g |
| Titanium oxide | 10 g |
| Red iron oxide | 0.3 g |
| Yellow iron oxide | 0.4 g |
| Brown iron oxide | 0.4 g |
| Chestnut iron oxide | 0.2 g |
| Cetyl stearyl alcohol oxyethylenated with 15 moles ethylene oxide | 7 g |
| Silicone oil (dimethyl polysiloxane having a viscosity of 20–22 degrees at room temperature) | 1 g |
| Polyglycol monostearate (m.w. polyglycol:400) | 6 g |
| Para-hydroxy acid ester | 0.2 g |
| Water, q.s.p. | 100 g |

EXAMPLE 27

A lotion is prepared by mixing the following ingredients:

| | |
|---|---|
| 3-(3,4-methylenedioxy benzylthio) 2-propionamido propionate of 3-[2-(2,4-dihydroxy 3,3-dimethyl butyramido)ethylthio]propylammonium | 0.25 g |
| Monohydrate of (diisobutylphenoxy-ethoxyethyl-dimethyl-benzyl) ammonium chloride | 0.75 g |
| Perfume | 0.05 g |
| 96° titer ethanol in water | 20.8 g |
| Water, q.s.p. | 100 g |

EXAMPLE 28

An aerosol foam is prepared by mixing the following ingredients in an aerosol bomb:

| | |
|---|---|
| Carboxyvinylpolymer-carboxypolymethylene, sold under the trade name "Carbopol 934" | 25 g |
| Magnesium ethoxylauryl sulfate | 8 g |
| Glycerol | 10 g |
| Ammonia | 0.2 g |
| 5-tetradecanamido 3-thia hexanedioate of di-(2-$\beta$-hydroxyethylthio ethylammonium) | 2 g |
| Water, q.s.p. | 100 g |

88 g of the above solution are packaged in an aerosol can with 12 g of difluorodichloromethane.

EXAMPLE 29

A thick hair lacquer of the following composition is prepared:

| | |
|---|---|
| Vinylacetate-crotonic acid copolymer, sold under the trade name "Resin 28.1310" (m.w. about 20,000) | 8 g |
| 2-amino 2-methyl 1-propanol | 0.8 g |

-continued

| | |
|---|---|
| 2-acetamido 3-p-fluorobenzylthio propionate of 2-hexadecylthio ethylammonium | 0.20 g |

EXAMPLE 30

A dye setting lotion of the following formula is prepared and used for application on white hair having a greasy appearance:

| | |
|---|---|
| Polyvinylpyrrolidone (P.V.P.)K value = 30, m.w. 40,000 | 0.4 g |
| Vinylacetate-crotonic acid copolymer (resin 28.1310 of National Starch) (m.w. 20,000) | 0.2 g |
| Ethanol, q.s.p. 50° | |
| 2-butyramido 3-isopropylthio propionate of 2-(2,6-dichlorobenzyl-thio) ethylammonium | 0.7 g |
| 1-aminopropylamioanthraquinone | 0.03 g |
| Picramic acid | 0.17 g |
| n-α-amino propylamino-4 N'--methyl-amino-1 anthraquinone | 0.040 g |
| Water | 100 g |

The pH value is adjusted to 7 by adding triethanolamine.

A good setting lotion is thus obtained which when applied on white hair, gives it a smoky gray shimmer while considerably improving its initial greasy appearance.

EXAMPLE 31

A shampoo is made in accordance with the invention by mixing:

| | |
|---|---|
| Technical (100%) triethanolamine lauryl sulfate | 5 g |
| Lauryl diethanolamide | 2 g |
| 5-m-chlorobenzamido 3-thia hexanedionate of di-[2-(5-nitro-2-pyridylthio) ethylammonium] | 2 g |
| Carboxymethyl cellulose | 0.25 |
| Perfume | 0.2 g |
| Water, q.s.p. | 100 g |

EXAMPLE 32

| | |
|---|---|
| Sodium lauryl sulfate oxyethylenated with 2.2 moles of ethylene oxide | 6 g |
| Pure mono lauryl sodium sulfosuccinate | 1 g |
| Lauryl diethanolamide | 2.5 g |
| Di-(5-amino 3-thia hexanedioate) of 3-thia-1,6-hexanediammonium | 5 g |
| Perfume | 0.3 g |
| Lactic acid, q.s.p. pH 6 | |
| Water, q.s.p. | 100 g |

EXAMPLE 33

A shampoo cream in accordance with the invention is prepared as follows:

| | |
|---|---|
| Sodium lauryl sulfate | 12 g |
| Product of the condensation of the fatty acids of copra with the methyltaurine, a paste sold under the trade name "Hostapon C.T." | 40 g |
| Lauryl monoethanolamide | 2 g |
| Glycerol monostearate | 4 g |
| 5-amino 3-thia hexanedioate of 2- | |
| (3-methane sulfonamido proylthio) ethylammonium | 3 g |
| Lactic acid, q.s.p. pH 6.5 | |
| Perfume | 0.2 g |
| Water, q.s.p. | 100 g |

EXAMPLE 34

A shampoo powder in accordance with the invention is prepared as follows:

| | |
|---|---|
| Sodium lauryl sulfate powder | 50 g |
| Product of the condensation of the fatty acids of copra with the sodium isethionate, sold under the trade name "Hostapon K.A." | 41 g |
| 2-formamido 3-(propyne 2-ylthio) propionate of 3-(1-naphthylthio) propylammonium | 8 g |
| Perfume | 1 g |

EXAMPLE 35

A shampoo powder is prepared as follows:

| | |
|---|---|
| Sodium lauryl sulfate powder | 40 g |
| Product of the condensation of fatty acids of copra with the sodium isethionate, sold under the trade name "Hostapon K.A." | 29 g |
| 2-butanesulfonamido 4-thia octanedioate of 2,2'-(2,3-dihydroxy-1,4-butanediyl dithio) diethylammonium | 20 g |
| Perfume | 1 g |

The powder of the two preceding examples can be dissolved in 10 times its weight of water and the resulting solution applied to the head.

EXAMPLE 36

A dye shampoo of the present invention is prepared as follows:

| | |
|---|---|
| di-[3-(2,2 ethylenedioxy ethylthio) 2-ureido propionate]of 2,2'-thio-diethylammonium | 5 g |
| Lauryl ammonium sulfate combined with 2 moles of ethylene oxide | 250 g |
| Copra diethanolamide | 50 g |
| Paratoluenediamine | 10 g |
| Methanediamino anisol sulfate | 0.5 g |
| Resorcinol | 5 g |
| Methaaminophenol | 1.5 g |
| Paraaminophenol | 1 g |
| Ethylenediamine tetracetic acid | 3 g |
| 40% sodium bisulfite | 15 g |
| Water, q.s.p. | 1000 g |

This product is mixed with 1000 g of hydrogen peroxide at 20 volumes and hair containing 80% white hair is impregnated therewith. A chestnut color results. The above shampoo composition has a pH range of 6.5 to 8.

EXAMPLE 37

The first stage, i.e., the reducing stage, of a permanent wave operation is achieved by using a cosmetic composition containing:

| | |
|---|---|
| Ammonium thioglycolate | 9.5 g |
| Fatty alcohol polyethoxy-ester (cetyl alcohol 30%-stearyl alcohol 70%), sold under the trade name of "Sipol Wax AO" | 0.8 g |
| Ammonia solution, q.s.p. 0.7 N | |

Thereafter, the hair while still rolled on curlers is neutralized by applying to the same the following neutralizing composition:

| | |
|---|---|
| Sodium bromate | 18 g |
| 2-amino 4-thia nonanedioate of 2-(3-hydroxypropylthio) ethylammonium | 0.5 g |
| Water, q.s.p. | 100 g |

After rinsing, the curlers are removed and the hair is then dried. A good permanent wave is obtained and the hair remained non-oily in appearance for a significantly longer time than did the hair when permanently waved using a cosmetic composition essentially as described above but without any 2-amino 4-thia nonanedioate of 2-(3-hydroxypropylthio) ethylammonium.

EXAMPLE 38

The first stage, i.e., the reducing stage, of a permanent waving operation is performed with a reducing composition containing:

| | |
|---|---|
| Ammonium thioglycolate | 9.5 g |
| Fatty alcohol polyethoxy-ester (cetyl alcohol 30% - stearyl alcohol 70%), sold under the trade name of "Sipol wax AO" | 0.8 g |
| Ammonia solution, q.s.p. 0.7 N | |
| Water, q.s.p. | 100 g |

A two package neutralizing composition is then employed, the first package containing:

| | |
|---|---|
| Hydrogen peroxide, q.s.p. | 6.6 volumes |
| Citric acid | 0.1 g |
| Water, q.s.p. | 100 g |
| and the second package containing: | |
| 5-amino 3-thia hexanedioate of 2-(3,4-dichlorobenzylthio) ethylammonium in powder form | 5 g |

Immediately prior to initiating the second stage of the permanent waving operation, i.e., the neutralizing stage, the powdered 5-amino 3-thia hexanedioate of 2-(3,4-dichloro benzylthio) ethylammonium is dissolved in the hydrogen peroxide solution. The hair, previously treated with the above reducing agent, being soft and pliable and still wound on curlers, is treated with the resulting neutralizing solution for a time sufficient to reform the disulphide bonds in the keratin of the hair.

After the hair has been rinsed, unwound from the curlers and dried, a permanent wave is obtained which exhibits good holding characteristics. Equally important, however, is that the hair remained non-oily in appearance for a significantly longer time than did the hair when permanently waved using essentially the same neutralizing composition but without the active compound.

V. Examples of Orally Administered Compositions

EXAMPLES 39–49

The following composition is prepared and is usefully employed to reduce excessive secretion of sebum on the scalp. It is orally administered in the form of drops.

| | |
|---|---|
| 2-amino 4-thia nonanedioate of 2-(3-hydroxypropylthio) ethylammonium | 1 g |
| Glycerin | 40 g |
| Ethyl alcohol | 30 g |
| Water, q.s.p. | 100 g |
| Lemon tincture (q.s.p. imparts a pleasing aroma) | |

The oral administration of this composition at a rate of 10 drops each day for 18 days by a person having greasy hair due to excessive secretion of sebum substantially improves the condition of the scalp and the appearance of the hair.

Essentially similar effective results are obtained when the above active compound is replaced with the following compounds:

5-amino 3-thia hexanedioate of 2-benzylthioethylammonium,
5-acetamido 3-thia hexanedioate of di-(2-benzylthioethylammonium),
5-amino 3-thia hexanedioate of 2-(2-alanylthio) ethylammonium,
5-amino 3-this hexanedioate of 2-methylthioethylammonium,
5-amino 3-thia hexanedioate of 3-benzylthio-propylammonium,
2-amino 4-thia heptanedioate of 2-benzylthio-ethylammonium,
5-amino 3-thia hexanedioate of 2-(2,2-dimethoxyethylthio)-ethylammonium,
2-acetamido 3-benzylthio propionate of 2-methylthioethylammonium,
5-benzamido 3–thia hexanedioate of di-(2-benzylthioethylammonium), and
5-nicotinamido 3-thia hexanedioate of di-(2-benzylthioethylammonium).

EXAMPLES 50–60

The following composition is prepared:

| | |
|---|---|
| 5-amino 3-thia hexanedioate of 2-(6-methyl 2-pyridylthio) propylammonium | 50 mg |
| Glucose | 300 mg |
| Water, q.s.p. | 5 ml |
| Orange juice (q.s.p. to impart a pleasant aroma) | |

Oral administration of this composition at the rate of 2 ampoules each day for 18 days by a person having greasy hair due to excessive secretion of sebum substantially improves the condition of the scalp and the appearance of the hair.

Essentially similar effective results are achieved by replacing 5-amino 3-thia hexanedioate of 2-(6-methyl 2-pyridylthio) propylammonium with the following compounds:

5-p-toluenesulfonamido 3-thia hexanedioate of di-(2-benzylthioethylammonium),
5-p-acetamidobenzenesulfonamido 3-thia hexanedioate of di-(2-benzylthioethylammonium),
5-p-acetamidobenzamido 3-thia hexanedioate of di-(2-benzylthioethylammonium),
5-p-acetamidobenzenesulfonamido 3-thia hexanedioate of di-(2-benzylthioethylammonium),
5-p-acetamidobenzamido 3-thia hexanedioate of di-(2-benzylthioethylammonium),
5-acetamido 3-thia hexanedioate of di 2-(2,4-dichlorobenzylthio) ethylammonium,
2-acetamido 4-thia heptanedioate of di-(2-methylthioethylammonium),
2-amino 4-thia decanedioate of 2-benzylthioethylammonium,
5-amino 3-thia hexanedioate of 2-benzylthio propylammonium, -continued 5-amino 3-thia hexanedioate of 2-benzylthio 2-methylpropylammonium,
5-amino 3-thia hexanedioate of phenylthio-2-ethyl-ammonium, and
5-amino 3-thia hexanedioate of 2-t-butylthioethyl-ammonium.

EXAMPLES 61-71

Lozenges for oral consumption having the following composition are prepared:

| | |
|---|---|
| 5-amino 3-thia hexanedioate of 2-octadecyl thio ethylammonium | 85 mg |
| Lactose | 300 mg |
| Powdered gum arabic | 100 mg |
| Simple syrup, q.s.p. | 500 mg. |

These lozenges, taken at a rate of 15 each day, by a person having greasy hair and scalp due to excessive secretion of sebum substantially improve the condition of the scalp and the appearance of the hair by reducing excessive secretion of sebum.

Essentially similar effective results are achieved by replacing the 5-amino 3-thia acid hexanedioate of 2-octadecylthio ethylammonium by the following compounds:

5-amino 3-thia hexanedioate of 2-tritylthioethylammonium,
5-amino 3-thia hexanedioate of 2-thenylthioethylammonium,
5-amino 3-thia hexanedioate of 2-(2-pyridylmethylthio) ethylammonium,
5-amino 3-thia hexanedioate of 2-(2-pyridylthio N-oxide) ethylammonium,
5-amino 3-thia hexanedioate of 2-(2-butenylthio) ethylammonium,
5-amino 3-thia hexanedioate of 2-(2-hydroxyethylthio)ethylammonium,
5-amino 3-thia hexanedioate of 2-(2,3-dihydroxypropylthio) ethylammonium,
3-benzylthio 2-phenylacetamido propionate of 2-methylthioethylammonium,
2-acetamido 3-tritylthiopropionate of 2-methylthioethylammonium, and
2-acetamido 3-benzhydrylthio propionate of 2-methylthioethylammonium.

EXAMPLES 72-82

Chewable pellets having the following composition are prepared:

| | |
|---|---|
| 3-methylthio 2-trifluoroacetamido propionate of 2-oleylthio ethylammonium | 5 g |
| Sucrose | 200 g |
| Lemon syrup | 50 g |

These pellets, administered at the rate of a coffee spoonful twice a day for a period of about 15 days to a person having greasy hair and scalp due to excessive secretion of sebum substantially reduce excessive secretion of sebum and thereby significantly improve the condition of the scalp and the appearance of the hair.

Essentially similar effective results are achieved by replacing 3-methylthio-2-trifluoroacetamido propionate of 2-oleyl thio ethylammonium by the following compounds:

5-amino 3-thia hexanedioate of 6-methanesulfonamido 6-ethoxycarbonyl 4-thia hexylammonium,
2-acetamido 4-thia nonanedioate of 2,2'-thio bis (ethylammonium),
di-(β-benzylthioethylammonium) p-acetamido-5 thia-3 hexanedioate,
5-amino 3-thia hexanedioate of 2-octadecylthio ethylammonium,
2-amino 4-thia heptanedioate of 2-undecenylthio ethylammonium,
2-amino 4-thia nonanedioate of 2-(3-hydroxypropylthio) ethylammonium,
di-(5-amino 3-thia hexanedioate) of 3-thia, 1,6-hexanediammonium,
2-amino 4-thia octanedioate of 2-(β-ureido ethylthio)-ethylammonium,
5-amino 3-thia hexanedioate of 2-(3-methanesulfonamido propylthio) ethylammonium, and
2-amino 4-thia decanedioate of 2-thenylthio ethylammonium.

EXAMPLES 83-97

Tablets having the following composition are prepared:

| | |
|---|---|
| 2-butanesulfonamido 4-thia octanedioate of 2,2'-(2,3-dihydroxy 1,4-butanediyl dithio) diethyl-ammonium | 10 mg |
| lactose | 150 mg |
| gum arabic | 100 mg |
| starch, q.s.p. | 500 mg |

These tablets, taken at a rate of 10 each day for 20 days by a person having greasy hair and scalp because of excessive secretion of sebum effectively reduce excessive sebum secretion and significantly improve the appearance of the hair and scalp condition.

Essentially similar effective results are achieved when the active compound is replaced by the following compounds:

5-amino 3-thia hexanedioate of 2-(p-phenylbenzylthio) ethylammonium,
5-tetradecanamido 3-thia hexanedioate of di-(2-β-hydroxyethylthio ethylammonium),
2-crotonamido 4-thia heptanedioate of di-(2-tertiobutylthio ethylammonium),
5-m-chlorobenzamido 3-thia hexanedioate of di-[2-(5-nitro 2-pyridylthio) ethylammonium],
2-butanesulfonamido 4-thia octanedioate of 2,2'-(2,3-dihydroxy, 1,4-butanediyl dithio) diethylammonium,
2-formamido 3-(2-propyne ylthio) propionate of 3-(1-naphthyl thio)propylammonium,
3-methylthio 2-trifluoracetamido propionate of 2-oleylthio ethylammonium,
di-[3-(2,2 ethylenedioxy ethylthio) 2-ureido propionate] of 2,2'-thio diethylammonium,
3-benzylthio 2-glutamino propionate of 2-tetrahydrofurfurylthio ethylammonium,
2-o-chlorobenzylthiomethyl 3-aza 4-oxo heptanedioate of 5,5'-sulfonyl bis(3-thia pentylammonium),
2-benzenesulfonamido 3-furfurylthio propionate of 2-(2,4-dichloro phenylthio) ethylammonium,
2-hexaneamido di-(p-methoxyphenyl) 3-methylthio propionate of 2-(2,3-dihydroxy propylthio) ethylammonium,
5-amino 3-thia hexanedioate of 2-(o-chlorobenzylthio) ethylammonium, and 5-amino 3-thia hexanedioate of 2-(p-bromobenzylthio) ethylammonium.

What is claimed is:

1. A composition for oral administration to a human having a scalp or skin characterized by an excessive secretion of sebum to improve the condition thereof by reducing said excessive secretion of sebum comprising in admixture with a solid ingestible carrier from 0.75 to 20 weight percent of a non-toxic active compound selected from the group consisting of:

5-amino-3-thia hexanedioate of 2-benzylthio-ethylammonium,
5-acetamido-3-thia-hexanedioate of di-(2-benzyl-thioethylammonium),
5-amino-3-thia hexanedioate of 2-(3-alanylthio) ethylammonium,
5-amino-3-thia hexanedioate of 2-methylthioethylammonium,
5-amino-3-thia hexanedioate of 3-benzylthiopropylammonium,
2-amino-4-thia heptanedioate of 2-benzylthioethylammonium,
5-amino-3-thia hexanedioate of 2-(2,2-dimethoxyethylthio)-ethylammonium,
2-acetamido-3-benzylthio-propionate of 2-methylthioethylammonium,
5-benzamido-3-thia-hexanedioate of di(2-benzylthioethylammonium),
5-p-toluenesulfonamido-3-thia-hexanedioate of di(2-benzylthioethylammonium),
5-p-acetamidobenzenesulfonamido-3-thia-hexanedioate of di-(2-benzylthioethylammonium),
5-p-acetamidobenzamido-3-thia-hexanedioate of di(2-benzylthioethylammonium),
2-acetamido-4-thia-heptanedioate of di(2-methylthioethylammonium),
2-amino-4-thia decanedioate of 2-benzylthioethylammonium,
5-amino-3-thia hexanedioate of 2-benzylthiopropylammonium,
5-amino-3-thia hexanedioate of 2-benzylthio-2-methylpropylammonium,
5-amino-3-thia hexanedioate of 2-phenylthioethylammonium,
5-amino-3-thia hexanedioate of 2-t-butylthioethylammonium,
5-amino-3-thia hexanedioate of 2-tritylthioethylammonium,
5-amino-3-thia hexanedioate of 2-(2-butenylthio) ethylammonium,
5-amino-3-thia hexanedioate of 2-(2-hydroxyethylthio)ethylammonium,
5-amino-3-thia hexanedioate of 2-(2,3-dihydroxypropylthio) ethylammonium,
3-benzylthio-2-phenylacetamido propionate of 2-methylthioethylammonium,
2-acetamido-3-tritylthiopropionate of 2-methylthioethylammonium,
2-acetamido-3-benzhydrylthio propionate of 2-methylthioethylammonium,
5-amino-3-thia hexanedioate of 6-methanesulfonamido-6-ethoxy carbonyl-4-thia hexylammonium,
2-acetamido-4-thia-nonanedioate of 2,2'-thio bis (ethylammonium),
di-(β-benzylthioethylammonium) 5-p-acetamido-3-thiahexanedioate,
5-amino-3-thia acid hexanedioate of 2-octadecylthio ethylammonium,
2-amino-4-thia heptanedioate of 2-undecenylthio ethylammonium,
2-amino-4-thia nonanedioate of 2-(3-hydroxypropylthio) ethylammonium,
di-(5-amino-3-thia hexanedioate) of 3-thia-1,6-hexanediammonium,
2-amino-4-thia octanedioate of 2-(β-ureido ethylthio)ethylammonium,
5-amino-3-thia hexanedioate of 2-(3-methanesulfonamido propylthio) ethylammonium,
5-amino-3-thia hexanedioate of 2-(p-phenylbenzylthio) ethylammonium,
5-tetradecanamido-3-thia hexanedioate of di(2-β-hydroxyethyl thio ethylammonium),
2-crotonamido-4-thia heptanedioate of di(2-tertiobutylthio ethylammonium),
2-butanesulfonamido-4-thia octanedioate of 2,2'-(2,3-dihydroxy-1,4-butanediyl dithio) diethylammonium,
2-formamido-3-(propyn-2-ylthio) propionate of 3-(1-naphthyl thio) propylammonium,
3-methylthio-2-trifluoroacetamido propionate of 2-oleylthio ethylammonium,
2-o-chlorobenzylthiomethyl-3-aza-4-oxo heptanedioate of 5,5'-sulfonyl bis (3-thia pentylammonium),
2-acetamido-3-p-methylthiophenylthio propionate of 2-(2,4,6-trimethyl benzylthio) ethylammonium,
5-amino-3-thia hexanedioate of 2-(3,4-dichlorobenzylthio) ethylammonium,
2-butyramido-3-isopropylthio propionate of 2-(2,6-dichlorobenzylthio) ethylammonium,
2-acetamido-3-(3-alanylthio) propionate of 2-m-fluorobenzylthio ethylammonium,
6-amino-3-thia heptanedioate of 2-p-dimethylaminobenzylthio ethylammonium,
2-hexanamido-di-(p-methoxyphenyl)-3-methylthio propionate of 2-(2,3-dihydroxy propylthio) ethylammonium,
5-amino-3-thia hexanedioate of 2-(o-chlorobenzylthio) ethylammonium,
5-amino-3-thia hexanedioate of 2-(p-bromobenzylthio) ethylammonium,
5-acetamido-3-thia hexanedioate of di-2-(2,4-dichlorobenzylthio) ethylammonium, and
2-acetamido-3-p-fluorobenzylthio propionate of 2-hexadecylthio ethylammonium.

2. The composition of claim 1 wherein the active compound is:
5-amino-3-thia hexanedioate of 2-benzylthio-ethylammonium.

3. The composition of claim 1 in dosage form which contains 10–75 mg of said active compound per unit dose.

4. A method for treating the scalp and skin, characterized by an excessive secretion of sebum, to improve the condition thereof by reducing said excessive secretion of sebum comprising orally administering to a human being having a scalp or skin so characterized the composition of claim 1.

5. The method of claim 4 wherein said composition is administered at a rate of about 1–5 mg/kg/day based on the weight of the human being for a time sufficient to reduce said excessive secretion of sebum.

6. The method of claim 5 wherein said composition is administered during a period of about 15 days.

* * * * *

UNITED STATES PATENT AND TRADEMARK OFFICE
CERTIFICATE OF CORRECTION

PATENT NO. : 4,151,301
DATED : April 24, 1979
INVENTOR(S) : Gregoire Kalopissis

It is certified that error appears in the above-identified patent and that said Letters Patent are hereby corrected as shown below:

In the Heading -

Under "[30] Foreign Application Priority Data"

add the following --

| | | |
|---|---|---|
| June 3, 1969 | Belgium | 74877 |
| June 21, 1967 | France | 111396 |
| July 28, 1967 | France | 116160 |
| January 29, 1964 | France | 961897 |

In the Heading, under "Related U. S. Application Data"

line 10, "June 14, 1969" should read

--June 14, 1968--.

Signed and Sealed this

First Day of January 1980

[SEAL]

Attest:

SIDNEY A. DIAMOND

Attesting Officer　　Commissioner of Patents and Trademarks